United States Patent [19]

Rottmaier et al.

[11] 4,170,701

[45] Oct. 9, 1979

[54] PROCESS FOR THE PREPARATION OF (THIO)HYDANTOINS MODIFIED WITH AMIDE GROUPS

[75] Inventors: Ludwig Rottmaier; Rudolf Merten, both of Leverkusen, Fed. Rep. of Germany

[73] Assignee: Bayer Aktiengesellschaft, Fed. Rep. of Germany

[21] Appl. No.: 897,666

[22] Filed: Apr. 19, 1978

[30] Foreign Application Priority Data

Apr. 22, 1977 [DE] Fed. Rep. of Germany ....... 2718103
May 18, 1977 [DE] Fed. Rep. of Germany ....... 2722513

[51] Int. Cl.² .............................................. C08G 18/00
[52] U.S. Cl. ......................................... 528/49; 528/68; 528/73; 548/310; 548/313
[58] Field of Search ............................ 528/73, 49, 68; 548/310, 313

[56] References Cited

U.S. PATENT DOCUMENTS

| | | | |
|---|---|---|---|
| 3,549,599 | 12/1970 | Merten | 528/68 |
| 4,089,860 | 5/1978 | Merten et al. | 548/310 |

*Primary Examiner*—Maurice J. Welsh
*Attorney, Agent, or Firm*—Connolly and Hutz

[57] ABSTRACT

Processes for the production of hydantoins substituted by amide groups wherein unsaturated cyclic imide compounds are reacted with primary amins and then with organic isocyanates.

15 Claims, No Drawings

PROCESS FOR THE PREPARATION OF (THIO)HYDANTOINS MODIFIED WITH AMIDE GROUPS

This invention relates to a process for the preparation of (thio)hydantoins modified with amide groups.

The preparation of hydantoins modified with amide groups is already known. These compounds are formed by the reaction of aspartic acid esters with isocyanates or isothiocyanates followed by cyclisation to hydantoin-5-acetic acid esters and by a reaction with amines in which alcohols are split off.

It has now been found that hydantoins which are substituted by amide groups, preferably in the 5-position can be obtained directly and in very high yields by reacting amines with maleic acid imides which may be substituted and which may be prepared in situ, and then leaving the resulting aspartic imides to react with the isocyanate or isothiocyanate and effecting ring closure under the influence of heat and catalyst.

The present invention therefore relates to a process for the preparation of (thio)hydantoins which are substituted with amide groups, wherein maleic acid imides represented by the following general formula (I)

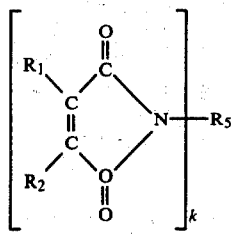

in which

R$_1$ and R$_2$, which may be the same or different, and represent hydrogen or an optionally substituted aliphatic group, R$_5$ represents hydrogen or an optionally substituted aliphatic, cycloaliphatic, aromatic, aliphatic-aromatic or heterocyclic group, and k represents an integer of from 1 to 3, preferably 1 or 2, are reacted with a primary monoamine or polyamine and the reaction product obtained is reacted with an organic mono- or polyiso(thio)cyanate and subsequently cyclised by heating, optionally in the presence of catalysts.

The maleic acid imides used for the process according to the invention are preferably imides represented by the general formula (I) in which R$_1$ and R$_2$ preferably represent hydrogen or a C$_1$ to C$_{18}$ alkyl group which may be substituted with halogen (chlorine, bromine), and R$_5$ preferably represents hydrogen; or a C$_1$ to C$_{20}$ alkyl group or C$_5$ to C$_{12}$ cycloalkyl group which both may be substituted by halogen, preferably chlorine or bromine, by a hydroxyl group, by a C$_1$ to C$_{18}$ alkoxy group or a C$_2$ to C$_{18}$ alkoxy carbonyl group, or a C$_6$ to C$_{16}$ aryl group which may be substituted by halogen, preferably chlorine or bromine, by nitro, by C$_1$ to C$_{18}$ alkyl, by C$_1$ to C$_{18}$ haloalkyl, by hydroxyl, by C$_1$ to C$_{18}$ hydroxy alkoxy, by C$_2$ to C$_{18}$ alkoxy carbonyl or by hydroxy carbonly groups; or a C$_7$ to C$_{18}$ aralkyl group or a C$_5$ to C$_{12}$ heterocyclic group containing N, O and-/or S atoms in the ring.

The heterocyclic groups are preferably aromatic or cycloaliphatic 5 or 6-membered rings containing one or more oxygen, nitrogen and/or sulphur atoms, e.g. groups derived from furan, pyridine, thiophene, imidazole, pyrimidine or piperazine. Most preferably, R$_5$ is hydrogen, a C$_1$ to C$_8$ alkyl group or a C$_6$ to C$_{16}$ aryl group such as phenyl, naphthyl or bisphenyl, or diphenyl groups which are linked through O, S, SO$_2$, CH$_2$, CH$_3$—C—CH$_3$ or CO.

The term "(thio)hydantoins" when used herein including the claims is intended to mean a member selected from the group consisting of hydantoins and thiohydantoins. Similarly, the term "iso(thio)cyanate" is intended to mean a member selected from the group consisting of isocyanates and thiocyanates.

Imides of maleic acid, such as maleic acid imide, N-methyl-maleic acid imide, N-butyl-maleic acid imide, N-phenyl-maleic acid imide or bis-maleic imides based on hexamethylene diamine, diamino diphenyl methane, phenylene diamine, tolylene diamine or naphthylene diamine are particularly preferred. Maleic acid imides are prepared from maleic acid amid by elimination of water. The method is well-known in the literature.

The mono- and polyamines used for the reaction according to the invention are preferably those represented by the following general formula (II)

in which

R$^3$ has the meaning of R$^5$ excluding hydrogen, and l represents an integer of from 1 to 3, preferably 1 or 2.

R$^3$ is most preferably derived from a C$_1$ to C$_{18}$ alkyl group, a C$_5$ to C$_6$ cycloalkyl group or a C$_6$ to C$_{16}$ aryl group such as a phenyl, naphthyl, bisphenyl or benzyl group or diphenyl groups linked together through O, S, SO$_2$ CH$_2$, CH$_3$—C—CH$_3$ or CO, which aryl group or groups may be optionally substituted by halogen, by C$_1$ to C$_3$ alkyl groups or by C$_1$ to C$_3$ alkyl groups or by C$_1$ to C$_3$ alkoxy groups. The amines are most preferably primary amines such as methylamine; ethylamine; butylamine; cyclohexylamine; ethylene diamine; propylene diamine; tetramethylene diamine; hexamethylene diamine, commercial mixtures of trimethyl hexamethylene diamine; 1,4-diamino cyclohexane, 1-aminomethyl-5-amino-1,3,3,-trimethyl-cyclohexane (isophorone diamine), 4,4'-diamino dicyclohexyl methane, ethanol amine, propanolamine, isopropanolamine, aniline, aminophenol, 3- and 4-aminobenzoic acid or esters thereof; benzylamine; m- and p-phenylene diamine; 2,4- and 2,6-diaminotoluene or their commercial mixtures; m- and p-xylylene diamine or their commercial mixtures; 1,5-naphthylene diamine; benzidine; 4,4'diamino diphenyl methane and their commercial isomeric mixtures; 2,2-bis-(4-aminophenyl)-propane or 4,4'-diamino diphenyl ether.

The mono(thio)isocyanates used according to the invention are aliphatic or aromatic compounds containing one isocyanate group in the molecule, which may be substituted by heteroatoms, e.g. alkyl isocyanates such as ethyl, methyl, butyl, dodecyl or stearyl isocyanate, aromatic substituted or unsubstituted monoisocyanates such as phenyl, tolyl, isopropyl, nonyl chloro, tetrachloro, pentachloro, benzyl or bromophenyl isocyanate or isocyanatobenzoic, phthalic or isophthalic acid ester, isocyanatobenzonitrile, cycloaliphatic isocyanates such as cyclohexyl isocyanate and unsaturated isocyanates such as allyl, oleyl or cyclohexenyl isocyanate.

The isocyanates used as starting components according to the invention may be aliphatic, cycloaliphatic, araliphatic, aromatic or heteroxyclic polyisocyanates, preferably diisocyanates (see Annalen, 562, pages 75 to 136) for example ethylene diisocyanate; tetramethylene-1,4-diisocyanate; hexamethylene-1,6-diisocyanate; dodecane-1,12-diisocyanate; cyclobutane-1,3-diisocyanate; cyclohexane-1,3- and -1,4-diisocyanate and any mixtures of these isomers 1-isocyanato-3,3,5-trimethyl-5-isocyanatomethyl-cyclohexane (Germany Auslegeschrift No. 1,202,785); hexahydrotolylene-2,4-diisocyanate and -2,6-diisocyanate and any mixtures of these isomers; hexahydrophenylene-1,3-diisocyanate and/or 1,4-diisocyanate; perhydro-2,4' and/or -4,4'-diphenylmethanediisocyanate; phenylene-1,3-diisocyanate and -1,4-diisocyanate; tolyene-2,4-diisocyanate and -2,6-diisocyanate and any mixtures of these isomers; diphenylmethane-2,4'-diisocyanate and/or 4,4'-diisocyanate; naphthalene-1,5-diisocyanate; triphenylmethane-4,4',4"triisocyanate; polyphenylpolymethylene polyisocyanates which can be obtained by aniline formaldehyde condensation followed by phosgenation and which have been described, for example, in British Patent Specifications No. 874,430 and No. 848,671; perchlorinated aryl polyisocyanates such as those described, for example, in German Auslegeschrift No. 1,157,601; polyisocyanates having carbodiimide groups as described in German Patent Specification No. 1,092,007; diisocyanates of the kind described in U.S. Pat. No. 3,492,330; polyisocyanates with allophanate groups as described e.g. in British Patent Specification No. 99,890 Belgian Patent Specification No. 761,626 and published Dutch Patent Application No. 7,102,522; polyisocyanates with isocyanurate groups, e.g. as described in German Patent Specification Nos. 1,022,789; 1,222,067 and 1,027,394 and in German Offenlegungsschriften Nos. 1,929,034 and 2,004,048; polyisocyanates with urethane groups as described e.g. in Belgian Patent Specification No. 752,261 or U.S. Pat. No. 3,394,164; polyisocyanates with acylated urea groups according to German Patent Specification No. 1,230,778; polyisocyanates with buiret groups as described e.g. in German Patent Specification No. 1,101,394; British Patent Specification No. 889,050 and French Patent Specification No. 7,017,514; polyisocyanates prepared by telomerisation reactions as described, for example, in Belgian Patent Specification No. 723,640; polyisocyanates having ester groups such as those mentioned, for example, in British Patent Specifications Nos. 965,474 and 1,072,956; U.S. Pat. No. 3,567,763 and German Patent Specification No. 1,231,688 and reaction products of the above mentioned isocyanates with acetylene according to German Patent Specification No. 1,072,385.

The distillation residues obtained from the commercial production of isocyanates and still containing isocyanate groups may also be used, optionally as solutions in one or more of the above mentioned polyisocyanates. Any mixtures of the above mentioned polyisocyanates may also be used.

Particularly suitable are the mono- and polyiso(thio)cyanates represented by the following general formula (III)

(III)

in which
R[4] has the same meaning as R[5] with the exclusion of hydrogen and with the exclusion of the substituents hydroxyl, hydroxy alkoxy and hydroxy carbonyl, and z represents an integer of from 1 to 3. preferably 1 or 2.

R[4] preferably represents an aliphatic group with 1 to 20 carbon atoms which may be substituted by halogen, by $C_1$ to $C_6$ alkyl and/or by $C_6$ to $C_{16}$ aryl groups, or an aromatic group with 6 to 16 carbon atoms, a cycloaliphatic group with 5 to 12 carbon atoms, an aliphatic aromatic group with 7 to 20 carbon atoms; or an aromatic or cycloaliphatic group with 5 to 12 carbon atoms containing heteroatoms such as N, O or S. Aliphatic groups with 2 to 12 carbon atoms and aryl groups with 6 to 12 carbon atoms, such as phenyl, tolyl, naphthaly, diphenylmethane, diphenylether, diphenyl or diphenyl groups linked together through S, $SO_2$, CO or $CH_3$—C—$CH_3$ are particularly preferred.

It is preferred to use commercially readily available mixtures of tolylene diisocyanates, m-phenylene diisocyanate, phenyl isocyanate and its substitution products as well as phosgenated condensates of aniline and formaldehyde which have a polyphenylene-methylene structure and the symmetric compounds 4,4'-diisocyanatodiphenyl methane, 4,4'-diisocyanate diphenyl ether, p-phenylene diisocyanate, 4,4'-diisocyanato diphenyl dimethyl methane, analogous hydroaromatic diisocyanates with 2–12 C-atoms such as hexamethylene diisocyanate, and diisocyanates derived from isophorone.

The isocyanates may be used in the free form or partly or completely in the form of isocyanate derivatives which are obtained from the reaction of isocyanates with compounds containing reactive hydrogen and which act as masked isocyanates under the reaction conditions.

The masked isocyanates used are preferably the acyl urea obtained from lactams such as caprolactam, and carbamic acid esters obtained from aromatic and aliphatic monohydroxy and polyhydroxy compounds, e.g. the carbamic acid esters represented by the following general formulae:

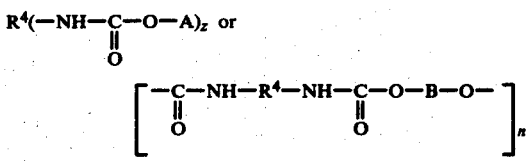

in which R[4] and z have the meaning already indicated and A represents the organic group of a monohydroxy compound or B represents the organic group of a bisfunctional or trisfunctional hydroxy compound, both A and B, the same or different, preferably an aliphatic group with 1 to 10 carbon atoms, a cycloaliphatic group with 5 to 10 carbon atoms, an aliphatic-aromatic group with 7 to 12 carbon atoms, or an aromatic group with 6 to 12 carbon atoms, any of which may be substituted by alkyl and/or aryl groups; and n represents an integer of from 1 to 1000, preferably 1 to 100.

Examples of such compounds include the carbamic acid esters of phenol, isomeric cresols, commercial mixtures thereof and similar aromatic hydroxyl compounds, aliphatic monohydric alcohols such as methanol, ethanol, propanol, isopropanol, butanol, isobutanol, diethylene glycol monomethyl ether, cyclohexanol and benzyl alcohol and of aliphatic diols and polyols such as ethylene glycol or trimethylol propane.

The urethanes may be introduced into the reaction as such or produced in situ by a reaction with alcohols.

Instead of the above mentioned mono- and polyisocyanates, the analogous (poly)isothiocyanates may be used.

The process according to the invention may be represented by the following equation:

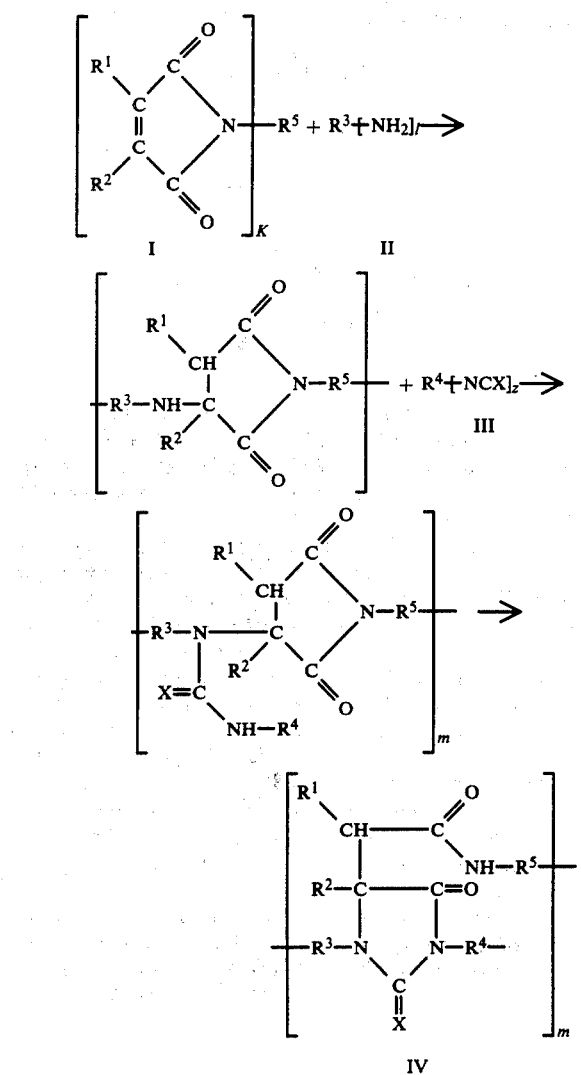

in which the groups
R$_1$ to R$_5$ have the meanings specified above and represent a monomolecular compound when
k, l and z=1, and a higher molecular compound when k and/or l and/or z>1; the hydantoin rings are linked through the groups R$_5$ and/or R$^3$ and/or R$^4$;
n represents an integer of from 1 to 1000, preferably 1 to 100.

The reaction between the maleic acid imides and amines is generally carried out at temperatures of from −20° C. to 200° C., preferably in an inert solvent and optionally in the presence of an effective quantity of an acid catalyst. The acid catalyst may also be used as solvent. Suitable acid catalysts include carboxylic acids such as acetic acid, butyric acid, pivalic acid, benzoic acid and trichloro acetic acid, phenol, cresols and phenols which have been acidified by electrophilic substitution.

The reaction between the amine-imides reaction product and the iso-(thio) cyanates is generally carried out at temperatures from −20° C. to 120° C., preferably at 20° C. to 80° C., optionally in inert solvents. The usual catalysts for amine-iso(thio) cyanate-addition may be used.

The inert solvents used are preferably aliphatic or aromatic hydrocarbons or their halogenation products, e.g. diisopropyl benzene, methyl naphthalene, di- or trichloro benzene or polar solvents such as N-methylpyrrolidone, dimethyl formamide, dimethyl acetamide, phenol, cresols or xylenols.

Cyclisation to the amide-containing hydantoins may be carried out in the presence of catalysts commonly used for the preparation of hydantoins, preferably triethylamine, dimethyl aniline, dabco (1,4-diazo-bicyclo-[2,2,2]-octane), acetic acid, pivalic acid, benzoic acid or metal catalysts such as boron trifluoride, titanium tetrabutylate or iron acetyl acetonate, and at temperatures of from 120° C. to 250° C., preferably 150° C. to 200° C. Reaction times of from 1 to 10 hours are generally required.

The reaction is generally carried out using stoichiometric quantities although one or other of the components may be used in excess in order to obtain polymers still containing reactive groups. The reaction products are worked up by the usual methods, e.g. by distillation or crystallisation processes. The polymer products may be directly stoved on metal sheets or wires in known manner or they may first be obtained in the pure form by precipitation, e.g. with acetone or methanol, and then processed, e.g. to foils.

The hydantoins with amide groups obtained according to the invention can be built into various polymers through the amide group and optionally, in the presence of other reactive groups, through the groups R$^3$, R$^4$ and R$^5$, in order to increase the temperature resistance of these polymers. For example, they may be reacted in this way with mono- or polycarboxylic acids or derivatives thereof or with monohydric or polyhydric alcohols to produce polyesters with increased heat resistance. The monohydantoins may be used as plant protective agents or as pharmaceutical products.

The polyhydantoins according to the invention are distinguished by their exceptionally high temperature resistance and they are suitable for use as adhesives, lacquers, foils and moulded products. Their properties may be varied within wide limits to make them suitable for the various fields of application by the addition of fillers, pigments and low molecular or high molecular weight components, e.g. they may be mixed with polyesters or polyamides to make them suitable for the manufacture of lacquers and foils.

EXAMPLE 1

1,3-diphenyl-5-(phenyl aminocarbonyl-methylene)-hydantoin 26.6 parts of the compound

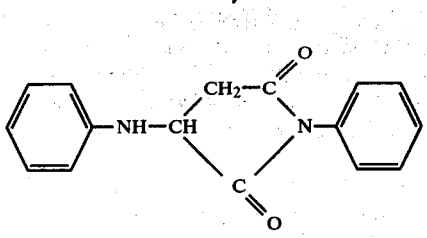

(from aniline and N-phenyl maleic imide) are dissolved in 100 ml of o-dichlorobenzene. 11.9 parts of phenylisocyanate are added and the reaction mixture is left to stand overnight. After the addition of 0.1 g of 1,4-diaza-bicyclo-[2,2,2]-octane, the solution is stirred for 6 hours at 175° C., the solvent is distilled off under vacuum and toluene is added to the residue. The crystalline precipitate obtained is suction filtered and recrystallised from ethyl acetate. The structure obtained by calculation is confirmed by the NMR- and IR-spectra (for hydantoin 1715 and 1770 cm$^{-1}$; for amide 1690 cm$^{-1}$).

Analysis: Calculated 71.6% C 4.93% H and 10.9% N; Found 71.7% C 5.1% H and 10.9% N.

EXAMPLE 2

1-cyclohexyl-3-phenyl-5-(phenyl aminocarbonyl-methylene)-hydantoin 17.3 parts of N-phenyl-maleic imide are dissolved in 50 parts of cresol. 9.9 parts of cyclohexylamine are added dropwise at 30°-35° C. After 2 hours stirring at room temperature, 11.9 g of phenylisocyanate are added and the solution is left to stand overnight. After a reaction time of 2 hours at 200° C., the solvent is distilled off under vacuum and the oily residue is dissolved in ethanol. 19.1 g of a crystalline precipitate are obtained after cooling. Its structure is confirmed by NMR- and IR-analysis (1705 and 1765 cm$^{-1}$ for hydantoin and 1690 cm$^{-1}$ for amide).

Analysis: Calculated: 70.6% C 6.38% H and 10.7% N; Found: 70.9% C 6.5% H and 10.6% N.

EXAMPLE 3

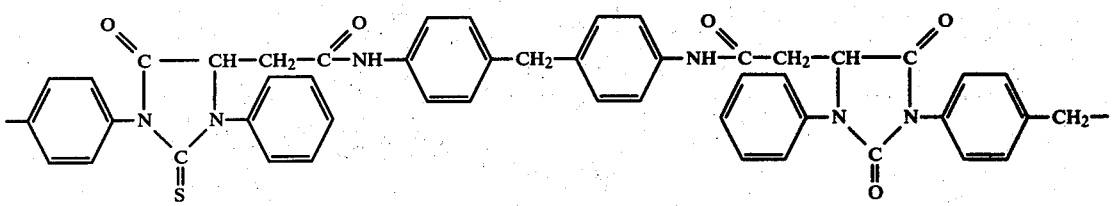

35.8 parts of the bisimide of maleic acid anhydride and 4,4'-diamino diphenylmethane are dissolved in 185 parts of cresol, 1.5 ml of acetic acid are added and the mixture is reacted with 18.6 parts of aniline at 120° C. for 15 hours.

25 parts of 4,4'-diisocyanate diphenylmethane are added to the resulting solution at 35°-40° C. and the mixture is left to stand overnight.

0.1 part of 1,4-diaza-bicyclo[2,2,2]-octane is added and the mixture is left to react for 6 hours at 200° C.

263 g of a 30% polyhydantoin-amide having the above identified recurring structural unit and a viscosity of 4900 cP at 25° C. are obtained. The IR-spectrum shows the characteristic bands for hydantoin at 1715 and 1770 cm$^{-1}$ and the characteristic band for amide at 1695 cm$^{-1}$. A lacquer film which has been stoved on a metal sheet is found to have good elasticity as well as good thermal properties.

EXAMPLE 4

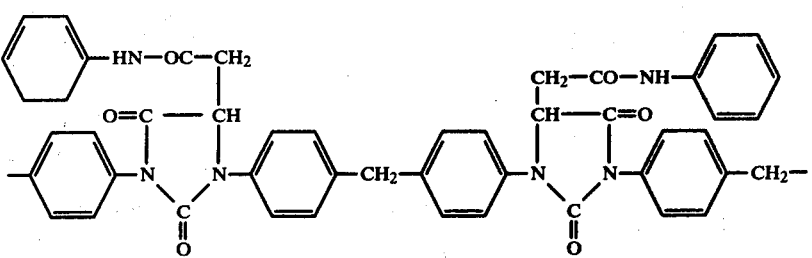

(a) 173 parts of N-phenyl maleic acid imide, 1 liter of acetic acid and 99 parts of 4,4'-diamino diphenyl methane are stirred together for 1 hour at 100° C. The precipitate obtained on cooling (175 parts) is suction filtered, washed and dried.

(b) 54.4 parts of the adduct prepared according to (a) are dissolved in 238 parts of cresol and reacted at 35°-40° C. with 25 g of 4,4'-diisocyanato diphenyl methane. The resulting solution is left to stand overnight. 0.1 g of diazo-bicyclo[2,2,2]-octane are added and the mixture is left to condense for 6 hours at 200° C. 316 g of a 25% amide-modified polyhydantoin having the above identified recurring structural unit and a viscosity of 700 cP at 25° C. are obtained. The IR-spectrum has the characteristic bands for hydantoin at 1730 and 1775 cm$^{-1}$ and for amide at 1695 cm$^{-1}$. An elastic lacquer film which has been stoved on a sheet metal has very good thermal properties.

We claim:

1. A process for the preparation of a (thio)hydantoin substituted by amide groups wherein a maleic acid imide represented by the following general formula I

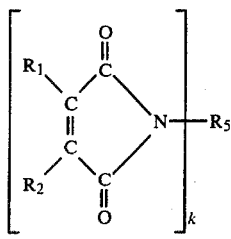 (I)

in which
R₁ and R₂, which may be the same or different, represent hydrogen or an optionally substituted aliphatic group,
R₅ represents hydrogen or an optionally substituted aliphatic, cycloaliphatic, aromatic, aliphatic-aromatic or heterocyclic group and
k represents an integer of from 1 to 3,
is reacted with a primary monoamine or polyamine, and the reaction product obtained is reacted with an organic mono- or polyiso(thio)cyanate and subsequently cyclised by heating.

2. A process as claimed in claim 1 wherein the reaction is carried out in the presence of a catalyst.

3. A process as claimed in claim 1 wherein
k represents 1 or 2,
$R_1$ and/or $R_2$ represents hydrogen or a $C_1$ to $C_{18}$ alkyl group which may be substituted with halogen, and
$R_5$ represents hydrogen, a $C_1$ to $C_{20}$ alkyl group, a $C_5$ to $C_{12}$ cycloalkyl group, a $C_6$ to $C_{16}$ aryl group, a $C_7$ to $C_{18}$ aralkyl group or a furan, pyridine, thiophene, imidazole, pyrimidine or piperazine group.

4. A process as claimed in claim 3 wherein R₅ represents hydrogen, a $C_1$ to $C_8$ alkyl group or a $C_6$ to $C_{16}$ aryl group.

5. A process as claimed in claim 1 wherein the mono- or poly-amine is a compound of the general formula (II)

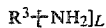 (II)

in which $R^3$ has the meaning of $R^5$ excluding hydrogen and
L represents an integer of from 1 to 3.

6. A process as claimed in claim 5 wherein L represents 1 or 2.

7. A process as claimed in claim 1 wherein the organic mono- or polyiso(thio)cyanate is a compound of the general formula (III)

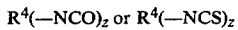 (III)

in which
$R^4$ has the same meaning as $R^5$, with the exclusion of hydrogen and the substitutents hydroxy, hydroxy alkoxy and hydroxyl carbonyl, and
z represents an integer of from 1 to 3.

8. A process as claimed in claim 7 wherein z represents 1 or 2, and $R^4$ represents an aliphatic group with 1 to 20 carbon atoms which may be substituted by halogen, by $C_1$ to $C_6$ alkyl or $C_6$ to $C_{16}$ aryl groups; or an aromatic group with 6 to 12 carbon atoms, a cycloaliphatic group with 5 to 12 carbon atoms, an aliphatic-aromatic group with 7 to 20 carbon atoms or an aromatic or cycloaliphatic group with 5 to 12 carbon atoms containing heteroatoms such as N, O and/or S.

9. A process as claimed in claim 1 wherein the reaction between the imide and the amine is carried out at a temperature of from −20° to 200° C.

10. A process as claimed in claim 1 wherein the reaction between the amine-imide and the iso(thio)cyanate is carried out at a temperature of from −20° to 120° C.

11. A process as claimed in claim 10 wherein the reaction between the amine-imide and the iso(thio)cyanate is carried out at a temperature of from 20° to 80° C.

12. A process as claimed in claim 1 wherein the reaction is carried out in an inert solvent.

13. A process as claimed in claim 1 wherein the cyclisation is carried out at a temperature of from 120° to 250° C.

14. A (thio)hydantoin produced by a process as claimed in claim 1.

15. An adhesive, laquer, foil or moulded product which comprises a (thio)hydantoin as claimed in claim 14.

* * * * *